(12) United States Patent
Motto-Ros et al.

(10) Patent No.: US 9,696,260 B2
(45) Date of Patent: Jul. 4, 2017

(54) DEVICE FOR TAKING SPECTROSCOPIC MEASUREMENTS OF LASER-INDUCED PLASMA

(71) Applicants: UNIVERSITE CLAUDE BERNARD LYON I, Villeurbanne (FR); CENTRE NATIONAL DE LA RECHERCHE SCIENTIFIQUE, Paris (FR)

(72) Inventors: Vincent Motto-Ros, Tartaras (FR); Jin Yu, Saint-Andre-de-Corcy (FR)

(73) Assignees: UNIVERSITE CLAUDE BERNARD LYON I, Villeurbanne (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/428,444

(22) PCT Filed: Sep. 25, 2013

(86) PCT No.: PCT/FR2013/052253
§ 371 (c)(1),
(2) Date: Mar. 16, 2015

(87) PCT Pub. No.: WO2014/049266
PCT Pub. Date: Apr. 3, 2014

(65) Prior Publication Data
US 2015/0226673 A1 Aug. 13, 2015

(30) Foreign Application Priority Data
Sep. 25, 2012 (FR) ...................... 12 59006

(51) Int. Cl.
*G01J 3/30* (2006.01)
*G01N 21/71* (2006.01)
(Continued)

(52) U.S. Cl.
CPC .......... *G01N 21/718* (2013.01); *G01J 3/0218* (2013.01); *G01J 3/443* (2013.01); *G01N 2201/0853* (2013.01)

(58) Field of Classification Search
CPC .... G01N 21/718; G01N 21/71; G01N 21/645; G01N 21/6458; G01J 3/02; G01J 3/443; G01J 3/4406
(Continued)

(56) References Cited

U.S. PATENT DOCUMENTS

| 3,603,688 | A | 9/1971 | Smith-Vaniz |
| 3,918,814 | A | 11/1975 | Weiser |

(Continued)

FOREIGN PATENT DOCUMENTS

| CN | 102128815 | 7/2011 |
| FR | 2 454 635 | 11/1980 |

(Continued)

OTHER PUBLICATIONS

De Giacomo et al., "Early stage . . . nanosecond-laser pulses", Spectrochimica Acta. Part B: Atomic Spectroscopy, vol. 60, No. 7-8, Aug. 31, 2005, pp. 935-947.

*Primary Examiner* — Abdullahi Nur
(74) *Attorney, Agent, or Firm* — Clark & Brody

(57) ABSTRACT

An installation for spectroscopic measurement includes a focusing system (2) for focusing a laser beam (3) on a sample (4) for analysis and a system (17) for collecting and spectroscopically analyzing light rays emitted by the plasma (15), this system (17) including, in particular, an optical fiber (18) for collecting light. The installation also includes a motor-driven system (23) for moving the optical fiber (18), an optical imaging system (25) for imaging the plasma in the form of an image, and a processor and control unit (24). The unit (24) is capable of analyzing the image formed by the optical imaging system in order to select a zone of interest and controlling the motor-driven system (23) in order to place the optical fiber in a position enabling it to collect light coming from the selected zone of interest in the plasma.

10 Claims, 2 Drawing Sheets

(51) Int. Cl.
*G01J 3/02* (2006.01)
*G01J 3/443* (2006.01)

(58) Field of Classification Search
USPC .................................................. 356/300–445
See application file for complete search history.

(56) References Cited

U.S. PATENT DOCUMENTS

| | | |
|---|---|---|
| 7,486,395 B2 | 2/2009 | Treado et al. |
| 7,599,048 B2 | 10/2009 | Yoo et al. |
| 2009/0273782 A1* | 11/2009 | Yoo .................. B23K 26/03 356/318 |
| 2010/0284003 A1 | 11/2010 | Hamilton |
| 2013/0046357 A1* | 2/2013 | Neev .................. A61N 5/022 607/45 |

FOREIGN PATENT DOCUMENTS

| | | |
|---|---|---|
| GB | 2 479 012 | 9/2011 |
| WO | 2009/043138 | 4/2009 |
| WO | 2009/137494 | 11/2009 |
| WO | 2014/027967 | 2/2014 |
| WO | 2014/049266 | 4/2014 |

\* cited by examiner

DEVICE FOR TAKING SPECTROSCOPIC MEASUREMENTS OF LASER-INDUCED PLASMA

The present invention relates to the field of qualitative and quantitative spectroscopic measurements of species or elements in a laser-induced plasma.

Laser-induced breakdown spectroscopy (LIES) consists essentially in striking a sample for analysis with a laser beam focused on its surface in order to generate a plasma by ablating of the sample. An installation using such a technique thus has a system for focusing a laser beam on a sample for analysis.

When the illuminance of the laser pulse is greater than the breakdown threshold of the sample for analysis, ablation takes place with a small quantity of material being vaporized in the form of a plasma. The excited species in the plasma, which may be ions, atoms, or molecules, emit characteristic lines that are detected by a collection and analysis system including in particular an optical fiber for collecting the light emitted by the plasma. The optical fiber is connected to a spectrometer that serves to analyze the collected spectrum in order to determine the concentrations of elements in the sample.

The advantages of the LIES technique include its versatility for analyzing samples of any form, solid, liquid, or gaseous, and without requiring any complex preparation, thus making it possible to analyze samples in situ. This technique also enables analysis to be performed in real time and makes it possible to measure samples that are situated remotely (typically at a distance lying in the range a few centimeters to about thirty meters).

Nevertheless, this technique presents poor performance in terms of measurement repeatability and reproducibility. It should be recalled that repeatability indicates the extent to which a measurement is stable over time when repeated a large number of times in the controlled conditions of the experiment. Reproducibility is indicative of the ability of an analytical technique to provide the same value for the same measurement being performed under different experimental conditions (which may or may not be controllable) and/or by different operators.

In the present state of its development, the LIES technique has reproducibilities that are rather poor being of the order of a few 10%, much greater than those available using more conventional analysis techniques where values are more of the order of one percent.

It is clear that the need for no or very little sample preparation makes the LIBS technique highly attractive, but this feature degrades its performance in terms of repeatability and reproducibility.

The poor performance that is obtained is intrinsically linked with the transient and non-point nature of the laser-induced plasma. The morphology or shape in time and space of the plasma fluctuates very greatly with changing experimental conditions. These fluctuations in the form of the plasma have a direct influence on the stability of the optical signal that is collected, thereby inevitably leading to deterioration in the repeatability and the reproducibility of measurements performed using the LIBS technique.

In the prior art, patent application CN 102128815 proposes a system for detecting the emission from the plasma by means of an optical fiber placed on an axis perpendicular to the incidence axis of the ablation laser beam. The transverse position of the fiber can be adjusted with the help of a two- or three-dimensional micrometer movement stage. Adjustment is performed manually so that the line of aim of the fiber passes through the center of the overall emission from the plasma. The optimum position for the setting is generally selected as the position that gives the best ratio of signal to background.

Although that technique seeks to optimize the position of the aiming point on the plasma used by the detection system, it does not take account of the non-uniform nature of the plasma and of experimental drifts induced by temperature variations, mechanical instabilities, or by the morphology of the sample itself. That technique does not make it possible to improve significantly the repeatability and the reproducibility of measurements.

In the prior art, the publication "Early stage emission spectroscopy study of metallic titanium plasma induced in air by femtosecond- and nanosecond-laser pulses" by A. De Giacomo, et al. describes a spectroscopic measurement installation comprising:

a focusing system for focusing a laser beam on a sample for analysis;
a system for collecting and spectroscopically analyzing light rays emitted by the plasma obtained under the effect of the sample being ablated by the laser beam, this collection and analysis system comprising in particular an optical fiber for collecting the light emitted by the plasma and connected to a spectrometer.

It also comprises:
a system for moving the optical fiber; and
an optical system for imaging the plasma in the form of an image.

Such an installation does not make it possible to take the morphology of the plasma into consideration since the plasma is considered as being a point source of emission. The fiber is positioned relative to the target on which the plasma is to be found.

The object of the present invention seeks to remedy the drawbacks of the prior art by proposing a novel installation for spectroscopic measurement performed on the basis of a laser-induced plasma, the installation being designed to provide active control over the position of the point from which the light emitted by the plasma is collected in order to improve significantly the repeatability and the reproducibility of measurements.

To achieve such an object, the spectroscopic measurement installation comprises:

a focusing system for focusing a laser beam on a sample for analysis;
a system for collecting and spectroscopically analyzing light rays emitted by the plasma obtained under the effect of the sample being ablated by the laser beam, this collection and analysis system comprising in particular an optical fiber for collecting the light emitted by the plasma and connected to a spectrometer.

According to the invention, the installation further comprises:

a motor-driven system for moving the optical fiber;
an optical imaging system for imaging the plasma in the form of an image; and
a processor and control unit connected to the motor-driven system for moving the optical fiber and to the optical system for imaging the plasma, the unit comprising:
means for analyzing the image formed by the optical imaging system in order to select a zone of interest; and means for controlling the motor-driven system in order to place the optical fiber in a position enabling it to collect light coming from the selected zone of interest in the plasma.

Furthermore, the installation of the invention may also present in combination one or more of the following additional characteristics:

- the optical system for imaging the plasma comprises an optical system for forming an image of the plasma and a camera having its output connected to the processor and control unit and adapted to capture the image of the plasma;
- the optical system for forming an image includes an optical collimator system independent of the main collimator system forming part of the system for collection and spectroscopic analysis, the independent optical collimator system being adapted to form the image of the plasma on the camera;
- the optical system for forming an image includes an optical collimator system branching from the main collimator system forming part of the system for collection and spectroscopic analysis, the branching optical collimator system forming the image of the plasma on the camera;
- the optical imaging system forms an image of the plasma and of at least a portion of the sample;
- the processor and control unit controls the motor-driven system for moving the optical fiber in at least two directions of the image plane formed by the main collimator system;
- the processor and control unit is connected to the laser beam processing system and includes means for synchronizing the emissions of the laser beam, the control of the movement system, and the acquisition of measurements by the spectrometer;
- the processor and control unit controls the spectrometer to acquire measurements after the movement system has been positioned in the appropriate position for collecting light beams coming from the zone of interest of the plasma;
- the processor and control unit controls the motor-driven movement system for a series of shots of the laser beam on a sample in such a manner as to keep the optical fiber always placed in the position that enables it to collect light coming from the same selected zone of interest; and
- a system for projecting a calibration reference into the plasma formation plane and in that the processor and control unit analyzes the calibration reference appearing in the image formed by the imaging optical system in order to calibrate the movement of the optical fiber.

Various other characteristics appear from the description made below with reference to the accompanying drawings, which show embodiments of the invention as non-limiting examples.

Figure 1:
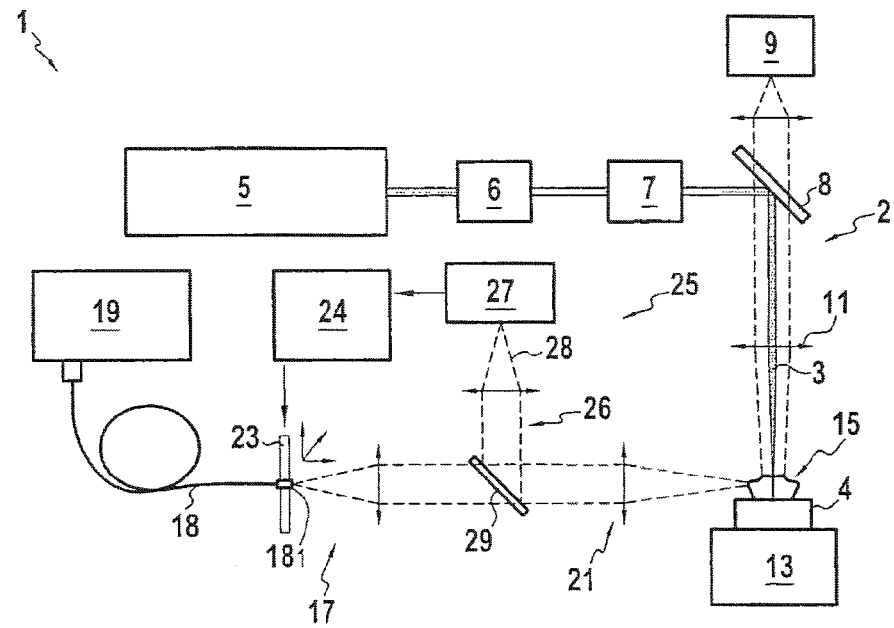
FIG. 1 is a diagrammatic view of an embodiment of a spectroscopic measurement installation in accordance with the invention.

As can be seen more clearly in FIG. 1, the invention provides a spectroscopic measurement installation (LIBS) 1.

This installation 1 has a system 2 for focusing a laser beam 3 on a sample 4 for analysis. The focusing system 2 comprises in conventional manner a pulse laser 5, e.g. of the Nd:YAG type. The wavelength of the light pulses delivered may be selected to lie in the infrared (IR) range (e.g. 1064 nanometers (nm)), in the visible range (e.g. 532 nm), or in the ultraviolet range (e.g. 355 nm or 266 nm). The pulse laser 5 preferably has a typical repetition rate of 10 hertz (Hz) with energy per pulse of the order of 30 millijoules (mJ).

The focusing system 2 also has an attenuator 6 and a shutter 7 placed on the light path of the laser beam 3 delivered by the laser 5. Opening and closing of the shutter 7 are synchronized with shots from the laser 5 and the acquisition of measurements.

In the example shown in FIG. 1, an optical reflector element 8 is arranged on the light path of the laser beam 3 so as to enable a monitoring camera 9 to be placed on the axis of the laser beam 3 directed towards the sample 4. By way of example, a lens 11 for focusing the laser beam 3 on the sample 4 is arranged between the optical reflection element 8 and the sample 4 for analysis.

In conventional manner, the sample 4 is positioned on a sample carrier 13, which is preferably motor-driven, enabling the sample 4 to be moved along three coordinates in three-dimensional space. Thus, the sample 4 can be moved with micrometer accuracy synchronously with the shots from the laser 5, with the beam of each laser pulse as focused on the sample leading to ablation of the sample 4 and to a small quantity of matter vaporizing in the form of a plasma 15.

The light rays emitted by the plasma 15 under the effect of the laser beam 3 ablating the sample 4 are recovered by a system 17 for collection and spectroscopic analysis including an optical fiber 18 for collecting the light emitted by the plasma. The optical fiber 18 is connected to a spectrometer 19 that can be of various types and that depends in practice on the selected application of the samples for analysis. In conventional manner, the spectrometer 19 serves to analyze the spectrum that has been selected and to determine the concentrations of elements in the sample 4.

The system 17 for collection and spectroscopic analysis also has a "main" collimator system 21 made up of one or more lenses providing optimized coupling of the light produced by the plasma 15 with the inlet $18_1$ of the optical fiber 18. The inlet $18_1$ of the optical fiber 18 is placed in the image plane of the main collimator system 21 which has the function of forming an image $I_1$ of the plasma through an optical assembly that should if possible be corrected for spherical and chromatic aberration. The aperture of the optical fiber 18 and its position in the image of the plasma determine the portion of the plasma from which light emission is picked up by the spectrometer 19. The sampled portion of the plasma can be optimized as a function of the optical acceptance of the spectrometer 19 by selecting the magnification of the main collimator system 21 and the aperture of the optical fiber 18. The main collimator system 21 possesses an optical axis that is selected to be perpendicular to the axis of incidence of the laser beam 3, which is perpendicular to the surface of the sample 4.

In accordance with the invention, the measurement installation 1 has a motor-driven system 23 for moving the optical fiber 18 at least in the image plane of the main collimator system 21. The motor-driven system 23 thus enables the end or the inlet $18_1$ of the optical fiber 18 to be moved along two Cartesian coordinate axes in the image plane. The motor-driven system 23 preferably also enables the end of the optical fiber 18 to be moved along the third Cartesian coordinate axis, i.e. along the optical axis of the main collimator system 21. The motor-driven system 23 may be implemented by any means known to the person skilled in the art. The accuracy and the stability of the positioning and the movements should be greater than the aperture of the optical fiber 18 by at least one order of magnitude, i.e. at micrometer scale.

The motor-driven system 23 is connected to a processor and control unit 24 adapted to control the movements of the motor-driven system 23. This processor and control unit 24 is connected to an optical system 25 for imaging the plasma 15 in the form of one or more images. This optical system 25 for imaging the plasma 15 in the form of one or more images includes an optical system 26 for forming an image $I_2$ of the plasma 15, and a camera 27.

The optical system 26 is thus adapted to form an image $I_2$ of the plasma on the camera 27, which is a matrix camera preferably of the charge-coupled device (CCD) type, and for example of the high dynamic range type. In the embodiment shown in FIGS. 1 and 2, the optical system 26 for forming an image comprises a collimator system 28 that branches from the main collimator system 21 and separator optics 29, taking a fraction (e.g. 10%) of the light from the main collimator system 21. The optical system 26 thus forms an image of the plasma at a location where it is possible to install the camera 27.

Advantageously, the images $I_1$ and $I_2$ formed respectively on the optical fiber 18 and on the optical system 26 are twin images correlated by the separator optics 29.

Contrary to the view commonly held by the person skilled in the art, who considers the plasma to be a point source of light emission, the invention considers the plasma as being an extended source of light emission. This extended emission source thus has a certain shape and a certain volume. Furthermore, in the invention, a plasma has internal structure that can vary over time and as a function of experimental fluctuations. Thus, detecting the plasma consists in detecting an extended emission source which involves the optical fiber capturing at least a portion of the emission in a manner that is localized in space and in time. In the invention, this capture $I_1$ by the optical fiber 18 is controlled with the help of the collimated image $I_2$ captured by the optical system 26.

It should be observed that it is possible to envisage imaging the plasma without taking a portion of the light used by the system 17 for collection and spectroscopic analysis, in order to avoid the attenuation that stems therefrom. In this variant embodiment, the optical system 26 for forming an image comprises a collimator optical system that is independent from the main collimator system 21 that forms part of the system 17 for collection and spectroscopic analysis, with the independent collimator system being adapted to form the image of the plasma on the camera 27. In this variant, the plasma is imaged along another axis perpendicular to the axis of the laser beam 3 using an optical collimator system that is independent. An image is thus obtained that is representative of but not necessarily identical to the image formed by the main collimator system 21. This variant embodiment is made possible because the plasma presents symmetry of revolution about the axis of incidence of the laser beam 3.

Furthermore, this variant embodiment is possible because, in the invention, the plasma is considered as being an extended light emission source.

In the invention, it is particularly advantageous to consider the plasma as being an extended emission source.

Since the morphology of the plasma varies over time, the invention makes it possible to position the fiber relative to the morphology of the plasma and not relative to the sample carrier 13 on which the sample 4 is to be found. The invention thus makes it possible advantageously to deal with fluctuations in the morphology of the plasma.

The processor and control unit 24 includes means for analyzing the image formed by the optical system 25 for imaging on the camera 27 in order to select a zone of interest in the image formed by the camera 27. The processor and control unit 24 has means for controlling the motor-driven system 23 in order to move the optical fiber 18 into a position that enables it to collect light from the selected zone of interest of the plasma.

The installation 1 of the invention makes it possible to control actively the position of the point from which the signal is taken from within the plasma 15. It is thus found to be possible to proceed with targeted detection, making it possible to detect always in the same portion of the plasma. Once it has been selected, this portion of the plasma is automatically aimed at by the optical fiber 18, with this being in spite of fluctuations in experimental conditions (laser, sample, ambient gas). If the shape of the plasma 15 changes, even by very little, the processor and control unit 24 controls the motor-driven system 23 for moving the fiber so as to correct immediately the position of the optical fiber 18 in order to ensure that it continuously tracks the shape of the plasma, and more precisely the selected zone of interest of the plasma.

Between different series of measurements, the optical fiber 18 is also positioned in order to compensate for all changes in the position and the morphology of the plasma. This automatic adjustment of the system relative to the plasma thus serves to compensate for all fluctuations in the shape of the plasma, in the short term and also in the long term. The repeatability and the reproducibility of measurements are thus significantly improved.

Figure 2:
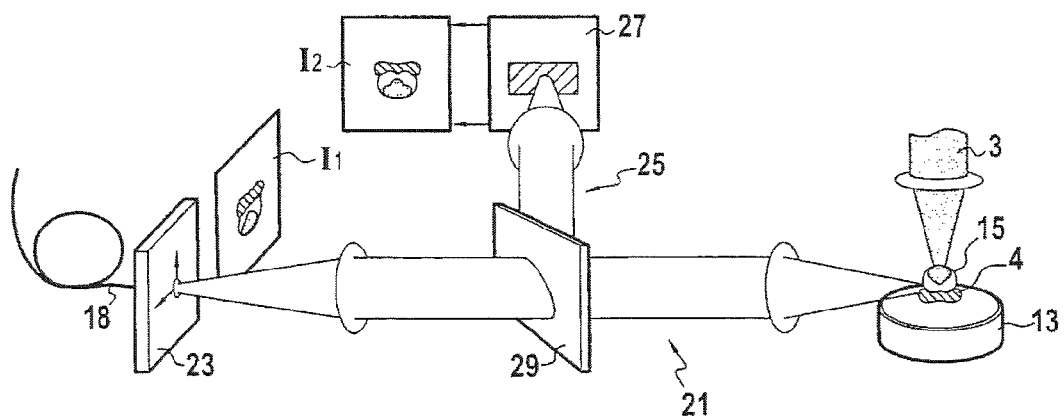
FIG. 2 is a diagrammatic view showing the operating principle of the installation in accordance with the invention.
Figure 3:
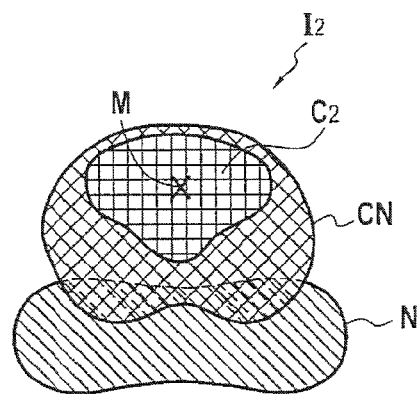
FIGS. 3 and 4 are examples of plasma images after the impact of the laser pulse on respective samples made of polymer and of aluminum.
Figure 4:
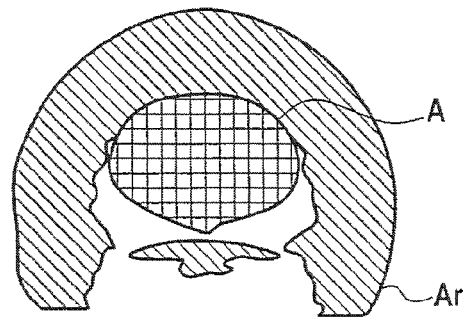

FIGS. 2 to 4 show in greater detail the advantages of the invention. As explained above, the main collimator system 21 that constitutes the main detection channel serves to form an image $I_1$ of the plasma 15 at the inlet $18_1$ of the optical fiber 18. The imaging optical system 25 serves to form an image $I_2$ of the plasma.

FIG. 3 shows an example of an image $I_2$ of a laser-induced plasma 15 showing the distribution of the species $C_2$, CN, and N at an instant 200 ns after the impact of the laser pulse on a sample 4 of polymer type in ambient air. In this image $I_2$, it can be seen that the plasma is not uniform and that different species are separated. Furthermore, it should be observed that the morphology of the plasma is extremely sensitive to experimental conditions and may fluctuate very considerably when experimental conditions change.

The invention seeks to overcome these fluctuations of plasma shape by always detecting the same zone of the plasma. For example, in the example shown in FIG. 3, the selected zone of interest or of measurement may be the center M of the zone for the species $C_2$. The processor and control unit 24 analyzes the image $I_2$ to identify this zone of interest in the image $I_2$. The processor and control unit 24 then compares the position of this zone of interest with the position of the inlet $18_1$ of the optical fiber 18. The processor and control unit 24 then controls the motor-driven system 23 to place the inlet $18_1$ of the optical fiber 18 in a position that enables it to aim at the zone of interest M of the plasma. In other words, the motor-driven system 23 is controlled by control signals that are proportional to the differences between the position of the optical fiber 18 and the position selected within the plasma, e.g. the point M at the center of the species $C_2$ in the plasma.

FIG. 4 shows another example of a non-uniform laser-induced plasma showing the distribution of Al and of Ar after 400 ns in a plasma induced on an aluminum sample under a controlled argon atmosphere. For example, the center of the Al species may be selected as being the zone of interest in the plasma.

In the examples of FIGS. 3 and 4, only the plasma appears in the images. It should be observed that provision may be made for the imaging optical system 25 to form an image of the plasma together with at least a portion of the sample 4.

It should be observed that the processor and control unit 24 is connected to the system 2 for focusing the laser beam and includes means for synchronizing the emission of the laser beam 3, the control of the movement system 23, and the acquisition of measurements by the spectrometer 19. It should be understood that the processor and control unit 24 detects the zone of interest M in the image $I_2$ and possibly controls the motor-driven system 23 at an appropriate speed so as to enable the optical fiber 18 to recover light coming from the zone of interest M of the plasma 15.

Naturally, the processor and control unit 24 causes the spectrometer 19 to acquire measurements after the movement system has been positioned in the appropriate position for collecting light beams coming from the zone of interest in the plasma.

Thus, for a series of laser beam shots on a sample, the processor and control unit 24 controls the motor-driven movement system 23 so as to keep the optical fiber 18 continuously in the position that enables it to collect light coming from the same selected zone of interest.

Figure 5:
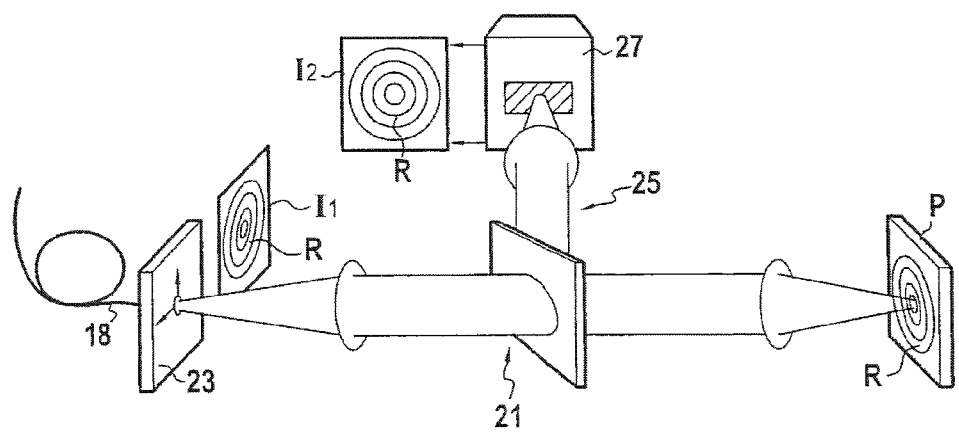
FIG. 5 is a diagram showing an example of calibration for the installation in accordance with the invention.

In an advantageous variant embodiment shown more particularly in FIG. 5, the installation 1 has a system for projecting a calibration reference R into the plane P where the plasma 15 is formed, shown diagrammatically in FIG. 5. In the invention, the processor and control unit 24 analyzes the calibration reference R that appears in the image formed by the imaging optical system 25 in order to calibrate the movement of the optical fiber 18. A calibration reference R may be created in the plane P where the plasma 15 is formed in any appropriate manner. An embodiment is shown in FIG. 5 in which a reflecting medium is positioned on the sample carrier 4 in correspondence with the plane P for forming the plasma 15. This reflecting medium is illuminated by a circular laser pointer that constitutes the calibration reference R. The calibration reference R is formed in the image plane of the main collimator system 21 and in the image plane for the plasma on the camera 27. Comparing the calibration references that appear in the images $I_1$ and $I_2$ makes it possible to calibrate the movement of the optical fiber 18 in the image plane of the main collimator system 21.

The invention is not limited to the examples described and shown since various modifications may be made thereto without going beyond its ambit.

The invention claimed is:

1. A spectroscopic measurement installation comprising:
   a focusing system (2) for focusing a laser beam (3) on a sample (4) for analysis;
   a system (17) for collecting and spectroscopically analyzing light rays emitted by the plasma (15) obtained under the effect of the sample being ablated by the laser beam, this collection and analysis system (17) comprising in particular an optical fiber (18) for collecting the light emitted by the plasma and connected to a spectrometer (19), the installation being characterized in that it further comprises:
   a motor for moving the optical fiber (18);
   an optical imaging system (25) for imaging the plasma in the form of an image; and
     an image analyzer for analyzing the image formed by the optical imaging system in order to select a zone of interest in the plasma; and
   a motor controller for controlling the motor in order to place the optical fiber in a position enabling it to collect light coming from the selected zone of interest in the plasma.

2. An installation according to claim 1, characterized in that the optical system (25) for imaging the plasma comprises an optical system (26) for forming an image of the plasma and a camera (27) having its output connected to the processor and control unit (24) and adapted to capture the image of the plasma.

3. An installation according to claim 2, characterized in that the optical system (26) for forming an image includes an optical collimator system independent of the main collimator system (21) forming part of the system (17) for collection and spectroscopic analysis, the independent optical collimator system being adapted to form the image of the plasma on the camera.

4. An installation according to claim 2, characterized in that the optical system (26) for forming an image includes an optical collimator system (28) branching from the main collimator system (21) forming part of the system (17) for collection and spectroscopic analysis, the branching optical collimator system (28) forming the image of the plasma on the camera (27).

5. An installation according to claim 1, characterized in that the optical imaging system (25) forms an image of the plasma and of at least a portion of the sample.

6. An installation according to claim 1, characterized in that the motor controller controls the motor-driven system (23) for moving the optical fiber in at least two directions of the image plane formed by the main collimator system (21).

7. An installation according to claim 1, further comprising a controller for synchronizing the emission of the laser beam, the control of the movement system, and the acquisition of measurements by the spectrometer (19).

8. An installation according to claim 1, characterized in that a controller controls the spectrometer (19) to acquire measurements after the movement system (23) has been positioned in the appropriate position for collecting light beams coming from the zone of interest of the plasma.

9. An installation according to claim 1, characterized in that the motor controller controls the motor-driven movement system (23), for a series of shots of the laser beam on a sample, in such a manner as to keep the optical fiber (18) always placed in the position that enables it to collect light coming from the same selected zone of interest.

10. An installation according to claim 1, characterized in that it includes a system for projecting a calibration reference into the plasma formation plane and in that a controller analyzes the calibration reference appearing in the image formed by the imaging optical system (25) in order to calibrate the movement of the optical fiber.

* * * * *